United States Patent [19]

Smothers

[11] Patent Number: 5,256,520
[45] Date of Patent: Oct. 26, 1993

[54] VISIBLE PHOTOSENSITIZERS FOR PHOTOPOLYMERIZABLE COMPOSITIONS

[75] Inventor: William K. Smothers, Hockessin, Del.

[73] Assignee: E. I. Du Pont de Nemours and Company, Wilmington, Del.

[21] Appl. No.: 974,195

[22] Filed: Nov. 10, 1992

Related U.S. Application Data

[62] Division of Ser. No. 810,997, Dec. 20, 1991, Pat. No. 5,204,467.

[51] Int. Cl.$^5$ .................. G03C 1/72; G03F 7/031
[52] U.S. Cl. .................. 430/281; 430/919; 430/920; 430/922; 430/923; 430/924; 430/2; 522/26; 522/28
[58] Field of Search .............. 430/281, 919, 920, 922, 430/923, 924, 2; 522/26, 28, 14, 16

[56] References Cited

U.S. PATENT DOCUMENTS

| | | | |
|---|---|---|---|
| 3,652,275 | 3/1972 | Baum et al. | 96/48 |
| 3,844,790 | 10/1974 | Chang et al. | 430/924 |
| 4,162,162 | 7/1979 | Dueber | 96/115 |
| 4,917,977 | 4/1990 | Smothers | 430/1 |
| 4,987,057 | 1/1991 | Kaji et al. | 430/919 |
| 4,987,230 | 1/1991 | Monroe | 546/94 |

OTHER PUBLICATIONS

R. Lemke, Arylidene Isophorones: Preparation and Properties of a Halocromic Polymethine System, Chem. Ber. 103, 1168–1170 (1970).

G. Kabas, The Condensation of Aromatic Aldehydes with Isophorone, Tetrahedron, 22, 1213–1218 (1966).

*Primary Examiner*—Christopher D. RoDee

[57] ABSTRACT

Photopolymerizable compositions containing photoinitiator systems that absorb in the visible are disclosed. The photopolymerizable compositions contain at least one ethylenically unsaturated monomer capable of free radical initiated addition polymerization and a photoinitiator system capable of being activated by actinic radiation. The photoinitiator system comprises a hexaarylbisimidazole, a chain transfer agent, and a sensitizer given by the formulae A or B wherein X and $R_1$–$R_{13}$ are as defined herein.

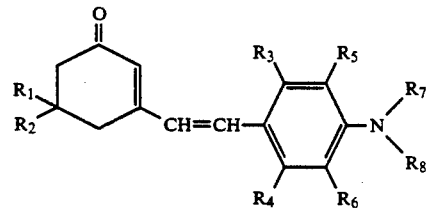

A

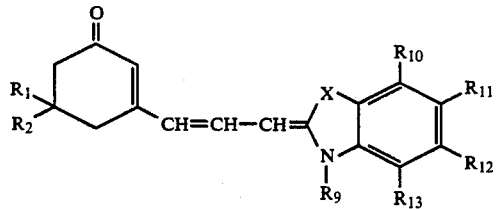

B

7 Claims, No Drawings

VISIBLE PHOTOSENSITIZERS FOR PHOTOPOLYMERIZABLE COMPOSITIONS

This is a division of application Ser. No. 07/810,997, filed Dec. 20, 1991, now U.S. Pat. No. 5,204,467.

FIELD OF THE INVENTION

This invention relates to photopolymerizable compositions containing photoinitiator systems that absorb in the visible. More particularly, this invention pertains to photopolymerizable compositions containing selected photodissociable initiators in combination visible sensitizers.

BACKGROUND OF THE INVENTION

Many of the conventional photoinitiators or photoinitiator systems are activatable primarily by radiation in the ultraviolet or shorter wavelength region (i.e., blue and green) of the visible spectrum. The availability of reliable, relatively inexpensive lasers which emit in the longer wavelength (i.e., red) region of the visible spectrum and which can be used as output devices for electronic imaging systems has made it desirable to develop photoinitiator systems which are activatable by this spectral region. Applications for photopolymerizable compositions containing these photoinitiator systems include graphic arts films, proofing, printing plates, photoresists, holograms, and holographic optical elements.

Photopolymerizable compositions containing 2,2',4,4',5,5'-hexaarylbisimidazoles, or HABI's, are well known. Sensitizers which extend the sensitivity of these compositions are disclosed, for example, in Baum, U.S. Pat. No. 3,652,275; Dueber, U.S. Pat. No. 4,162,162; Smothers, U.S. Pat. No. 4,917,977; and Monroe, U.S. Pat. No. 4,987,230. However, despite the advances which have been made, there is a continuing need for photoinitiator systems which are sensitive to the visible region of the spectrum.

SUMMARY OF THE INVENTION

The invention is a photopolymerizable composition comprising:
(1) at least one ethylenically unsaturated monomer capable of free radical initiated addition polymerization; and
(2) a photoinitiator system, capable of being activated by actinic radiation, said photoinitiator system comprising:
  (a) a hexaarylbisimidazole;
  (b) a chain transfer agent;
  (c) a sensitizer, said sensitizer selected wherein:

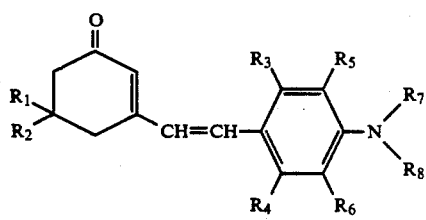

wherein:
$R_1$ and $R_2$ are independently alkyl from 1 to 4 carbon atoms;

$R_3$ and $R_4$ are independently hydrogen, alkyl of 1 to 6 carbon atoms, or alkyoxyl of 1 to 6 carbon atoms;

$R_5$ is hydrogen or methyl and $R_7$ is alkyl from 1 to 6 carbon atoms, or $(R_5+R_7)$ are $-(CH_2)_2-$ or $-(CH_2)_3-$;

$R_6$ is hydrogen or methyl and $R_8$ is alkyl from 1 to 6 carbon atoms, or $(R_6+R_8)$ are $-(CH_2)_2-$ or $-(CH_2)_3-$, with the proviso that $(R_5+R_7)$ and, $(R_6+R_8)$ may not be $-(CH_2)_2-$ at the same time; and

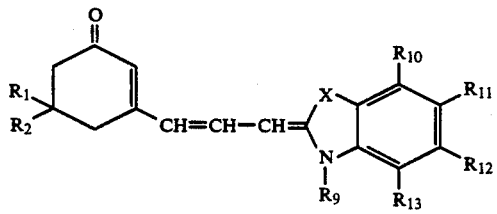

wherein:
$R_1$ and $R_2$ are independently alkyl from 1 to 4 carbon atoms;

X is O, S, $NR_{14}$, or $CR_{15}R_{16}$, where $R_{14}$, $R_{15}$, and $R_{16}$ are each an alkyl group of 1 to 6 carbon atoms or substituted or unsubstituted phenyl;

$R_9$ is a substituted or unsubstituted alkyl group of 1 to 7 carbon atoms or substituted or unsubstituted phenyl;

$R_{10}$, $R_{11}$, $R_{12}$, and $R_{13}$ are each independently hydrogen, substituted or unsubstituted alkyl and alkyoxyl of 1 to 6 carbon atoms, halogen, or substituted or unsubstituted phenyl; or ($R_{10}$ and $R_{11}$), ($R_{11}$ and $R_{12}$), or ($R_{12}$ and $R_{13}$) are joined to form a six-membered substituted or unsubstituted aromatic ring;

wherein said photoinitiator system is present in an amount sufficient to initiate polymerization of said monomer on exposure to actinic radiation.

In a preferred embodiment, $R_1$ and $R_2$ are methyl. In a more preferred embodiment $(R_5+R_7)$ and $(R_6+R_8)$ are $-(CH_2)_3-$. In another more preferred embodiment X is O, S, or $CR_{15}R_{16}$, $R_{15}$ and $R_{16}$ are each methyl; $R_9$ is methyl or ethyl; and $R_{10}$, $R_{11}$, $R_{12}$, and $R_{13}$ are each hydrogen. In a preferred embodiment, the composition contains a binder.

DETAILED DESCRIPTION OF THE INVENTION

Photopolymerizable Compositions

The novel compositions of this invention are photopolymerizable compositions in which polymerization is initiated by free radicals generated by actinic radiation. As described herein, these compositions comprise a sensitizer; a hexaarylbisimidazole; a polymerizable monomer; a chain transfer agent; and, optionally, a binder. The composition may also comprise other ingredients which are conventional components of photopolymerizable systems.

Sensitizers

One class of sensitizers is represented by:

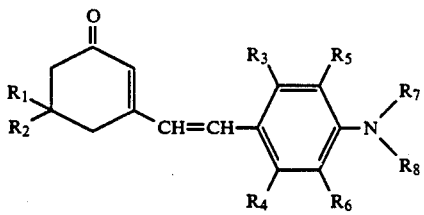

wherein:

$R_1$ and $R_2$ are independently alkyl from 1 to 4 carbon atoms;

$R_3$ and $R_4$ are independently hydrogen, alkyl of 1 to 6 carbon atoms, or alkyoxyl of 1 to 6 carbon atoms;

$R_5$ is hydrogen and $R_7$ is alkyl from 1 to 6 carbon atoms, or $(R_5+R_7)$ are —$(CH_2)_2$— or —$(CH_2)_3$—;

$R_6$ is hydrogen and $R_8$ is alkyl from 1 to 6 carbon atoms, or $(R_6+R_8)$ are —$(CH_2)_2$— or —$(CH_2)_3$—, with the proviso that $(R_5+R_7)$ and $(R_6+R_8)$ may not be —$(CH_2)_2$— at the same time.

In the preferred sensitizers of this class $R_1$ and $R_2$ are methyl. Sensitizers of this class include sensitizers S-1 and S-2 in which $R_5$ and $R_6$ are hydrogen and $R_7$ and $R_8$ are each methyl or ethyl.

In a more preferred class of sensitizers $(R_5+R_7)$ and $(R_6+R_8)$ are —$(CH_2)_3$—. A preferred member of this class is sensitizer S-6, in which $R_3$ and $R_4$ are hydrogen.

Another class of sensitizers is represented by:

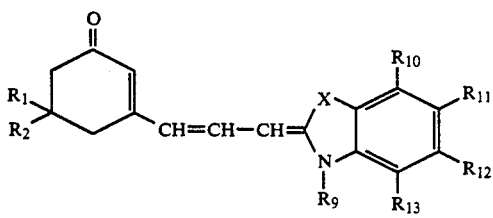

wherein:

$R_1$ and $R_2$ are independently alkyl from 1 to 4 carbon atoms;

X is O, S, $NR_{14}$, or $CR_{15}R_{16}$, where $R_{14}$, $R_{15}$, and $R_{16}$ are each an alkyl group of 1 to 6 carbon atoms or substituted or unsubstituted phenyl;

$R_9$ is a substituted or unsubstituted alkyl group of 1 to 7 carbon atoms or substituted or unsubstituted phenyl;

$R_{10}$, $R_{11}$, $R_{12}$, and $R_{13}$ are each independently hydrogen, substituted or unsubstituted alkyl and alkyoxyl of 1 to 6 carbon atoms, halogen, or substituted or unsubstituted phenyl; or ($R_{10}$ and $R_{11}$), ($R_{11}$ and $R_{12}$), or ($R_{12}$ and $R_{13}$) are joined to form a six-membered substituted or unsubstituted aromatic.

In a preferred class $R_1$ and $R_2$ are methyl. In a more preferred class of sensitizers X is O, S, or $CR_{15}R_{16}$, where $R_{15}$ and $R_{16}$ are each methyl; $R_9$ methyl, ethyl, or benzyl; $R_{10}$, $R_{11}$, $R_{12}$, and $R_{13}$ are each independently hydrogen, methyl, methoxy, or chloro. In a even more preferred embodiment $R_{15}$ and $R_{16}$ are each methyl; $R_9$ is methyl or ethyl; and $R_{10}$, $R_{11}$, $R_{12}$, and $R_{13}$ are each hydrogen. Representative sensitizers of this class are sensitizers, S-3, S-4, and S-5.

Where substitution is possible, any of the aliphatic or aromatic groups present in the sensitizers may be substituted by any of the well-known organic substituents provided the presence of the substituents does not adversely affect the properties of the sensitizer or of the photopolymerizable system needed for the operation of the invention. These properties include, for example, the solubility, absorption spectrum, and stability of the sensitizer. In addition, the presence of the substituent should not cause the sensitizer to adversely affect the stability of the photopolymerizable composition in which it is present.

Such substituents include for example: halogen, such as, for example, chlorine, bromine, and fluorine; cyano; alkoxy, such as, for example, methoxy, ethoxy, 2-ethoxyethoxy, and benzyloxy; aryloxy, such as, for example, phenoxy, 3-pyridyloxy, 1-naphthyloxy, and 3-thenyloxy; acyloxy, such as, for example, acetoxy, benzyloxy, and phenylacetoxy; aryloxycarbonyl, such as, for example, phenoxycarbonyl; alkoxycarbonyl, such as, for example, methoxycarbonyl; sulfonyl such as, for example, methanesulfonyl and p-toluenesulfonyl; carbamoyl, such as, for example, N-phenylcarbamoyl; acyl, such as, for example, benzoyl and acetyl; acylamido, such as, for example, p-toluenesulfonamido, benzamido, and acetamido; alkylamino, such as, for example, diethylamino, ethylbenzylamino, and i-butylamino; arylamino, such as, for example, anilino and diphenylamino. The aryl groups may also be substituted with substituted or unsubstituted alkyl groups, such as, for example, methyl, ethyl, cyclopentyl, 2-ethoxyethyl, benzyl, etc.

The sensitizers of this invention may be used individually or in combination with other members of the same class of sensitizers or with other sensitizing compositions, such as the sensitizers disclosed in Baum, U.S. Pat. No. 3,652,275, Dueber, U.S. Pat. Nos. 4,162,162 and 4,454,218, Smothers, U.S. Pat. No. 4,917,977, and Monroe, U.S. Pat. No. 4,987,230. The use of two or more, such compositions effects sensitization over a broader spectral range to match a variety of laser output radiation.

Hexaarylbisimidazoles

The sensitizers of this invention are used in conjunction with a 2,2',4,4',5,5'-hexaarylbisimidazole, or HABI. These compounds, which dissociate on exposure to actinic radiation to form the corresponding triarylimidazolyl free radicals have been described in: Chambers, U.S. Pat. No. 3,479,185; Cescon, U.S. Pat. No. 3,784,557; Dessauer, U.S. Pat. No. 4,252,887 and U.S. Pat. No. 4,311,783; Tanaka, U.S. Pat. No. 4,459,349, Wada, U.S. Pat. No. 4,410,621, Sheets, U.S. Pat. No. 4,662,286 and Sato, U.S. Pat. No. 4,760,150. The hexaarylbisimidazoles absorb maximally in the 255-275 nm region of the spectrum, and usually show some, though lesser, absorption in the 300-375 nm region. Although the absorption bands tend to tail out to include wavelengths as high as 430 nm, in the absence of a sensitizer these compounds normally require light rich in the 255-375 nm region of the spectrum for their dissociation.

Preferred HABI's are 2-o-chlorosubstituted hexaphenylbisimidazoles in which the other positions on the phenyl radicals are unsubstituted or substituted with fluoro, chloro, bromo, methyl or methoxy. These compounds are disclosed in Cescon, U.S. Pat. No. 3,784,557 and Dessauer, U.S. Pat. No. 4,252,887. Representative HABI'S include: o-Cl-HABI, i.e., biimidazole, 2,2'-bis(o-chlorophenyl)-4,4,'5,5'-tetraphenyl-; CDM-HABI, i.e., 2-(o-chlorophenyl)-4,5-bis(m-methoxyphenyl)-imidazole dimer; TCTM-HABI, i.e., 1H-imidazole, 2,5-bis(o-chlorophenyl)-4-[3,4-dimethoxyphenyl]-, dimer;

2,4-DCl-HABI, i.e., biimidazole, 2,2'-bis[2,4-dichlorophenyl]-4,4',5,5'-tetraphenyl-; 2,3-DCl-HABI, i.e., biimidazole, 2,2'-bis[2,3-dichlorophenyl]-4,4',5,5'-tetraphenyl-; 2,3,5-TCl-HABI, i.e, biimidazole, 2,2'-bis[2,3,5-trichlorophenyl]-4,4',5,5'-tetraphenyl-; and the imidazole dimers disclosed in Sheets, U.S. Pat. No. 4,662,286.

Chain Transfer Agents

Generally, one or more coinitiators consisting of a hydrogen atom donor, chain transfer agent, leuco dye, or electron donor are used with the 2,4,5-triarylimidazole dimers and dye sensitizer. Useful coinitiators are disclosed in Chambers, U.S. Pat. No. 3,479,185 and Smothers, U.S. Pat. No. 4,994,347. Suitable chain transfer agents include organic thiols, such as 2-mercaptobenzothiazole, 2-mercaptobenzoxazole, and 2-mercaptobenzimidazole. Others which can be used include various tertiary amines known in the art, N-phenylglycine, and 1,1-dimethyl-3,5-diketocyclohexane. Except for systems which contain N-vinyl carbazole monomer, the preferred chain transfer agents are N-phenyl glycine, 2-mercaptobenzoxazole and 2-mercaptobenzthiazole. For photopolymerizable compositions which contain the monomer N-vinyl carbazole, the preferred chain transfer agents are: 5-chloro-2-mercaptobenzothiazole; 2-mercaptobenzothiazole; 1-H-1,2,4-triazole-3-thiol; 6-ethoxy-2-mercaptobenzothiazole; 4-methyl-4H-1,2,4-triazole-3-thiol; and 1-dodecanethiol.

Monomers/Binders

The composition contains at least one ethylenically unsaturated compound, generally known as a monomer, which undergoes free-radical initiated polymerization to form a high molecular weight compound. The composition contains at least one such material and may contain a mixture of such materials. In general, preferred monomers for photopolymer applications have boiling points greater than 100° C., more preferably, greater than 150° C.

Typical monomers are: unsaturated esters of alcohols, preferably polyols, such as, diethylene glycol diacrylate, glycerol triacrylate, ethylene glycol dimethacrylate, pentaerythritol tri- and tetraacrylate and methacrylate; unsaturated amides, such 1,6-hexamethylene bis-acrylamide; vinyl esters such as divinyl succinate, divinyl phthalate, and divinyl benzene-1,3-disulfonate; styrene and derivatives thereof; and N-vinyl compounds, such as N-vinyl carbazole. Numerous other unsaturated monomers polymerizable by free-radical initiated polymerization and useful in photopolymerizable compositions are known to those skilled in the art. For photoresist applications the preferred monomers are trimethylol propane triacrylate, the triacrylate ester of ethoxylated trimethylolpropane, tetraethylene glycol diacrylate, and tetraethylene glycol dimethacrylate.

The binder is an optional component present in the preferred photopolymerizable compositions of this invention. The binder is a preformed macromolecular polymeric or resin material. In general, the binder should be soluble in the coating solvent and compatible with the other components of the photopolymerizable system. Representative binders are poly(methyl methacrylate) and copolymers of methyl methacrylate with other alkyl acrylates, alkyl methacrylates, methacrylic acid, and/or acrylic acid; poly(vinyl acetate) and its partially hydrolyzed derivatives; gelatin; cellulose esters and ethers, such as cellulose acetate butyrate; and polyethylene oxides. Numerous other binders useful in photopolymerizable compositions are known to those skilled in the art. Lists of representative monomers and binders useful in photopolymerizable compositions are given in Ishikawa, U.S. Pat. No. 4,481,276.

Photopolymerizable compositions useful for recording holograms are disclosed in Haugh, U.S. Pat. No. 3,658,526; Chandross, U.S. Pat. No. 3,993,485; and Fielding, U.S. Pat. Nos. 4,535,041 and 4,588,664. Preferred compositions are disclosed in Keys, U.S. Pat. No. 4,942,102; Monroe, U.S. Pat. No. 4,942,112; Smothers, U.S. Pat. No. 4,959,284; and Trout, U.S. Pat. No. 4,963,471. In the preferred compositions either the monomer or the binder comprises one or more moieties selected from the group consisting of (1) aromatic moieties selected from the group consisting of (i) substituted or unsubstituted phenyl, (ii) substituted or unsubstituted naphthyl, and (iii) substituted or unsubstituted heterocyclic aromatic moieties having up to three rings; (2) chlorine; (3) bromine, and mixtures thereof; and the other constituent is substantially free of said moiety or moieties. Compositions in which the monomer contains said moiety are more preferred.

For systems in which the monomer contains said moiety and the binder is free of said moiety, preferred liquid monomers are: 2-phenoxyethyl acrylate, 2-phenoxyethyl methacrylate, phenol ethoxylate monoacrylate, 2-(p-chlorophenoxy)ethyl acrylate, p-chlorophenyl acrylate, phenyl acrylate, 2-phenylethyl acrylate, 2-(1-naphthyloxy)ethyl acrylate, o-biphenyl methacrylate, o-biphenyl acrylate, ethyl 1-benzoyl-2-vinyl-1-cyclopropane carboxylate and mixtures thereof. Preferred solid monomers, which may be used to advantage in combination with liquid monomers are: N-vinyl carbazole; 2,4,6-tribromophenyl acrylate or methacrylate; pentachlorophenyl acrylate or methacrylate; 2-naphthyl acrylate or methacrylate; 2-(2-naphthyloxy)ethyl acrylate or methacrylate; and mixtures thereof. Preferred binders for these systems are: cellulose acetate butyrate; poly(methyl methacrylate); poly(vinyl butyral); poly(vinyl acetate); and fluorine containing binders containing 3 to 25% by weight fluorine, such as copolymers of vinyl acetate with tetrafluoroethylene and/or hexafluoropropylene. For reflection holograms, the preferred binders are poly(vinyl butyral), poly(vinyl acetate), and copolymers of vinyl acetate with tetrafluoroethylene and/or hexafluoropropylene containing 3 to 25% by weight fluorine, such as, for example, the 82:18 (mole%) vinyl acetate/tetrafluoroethylene copolymer. For systems in which the binder contains said moiety and the monomer is free of said moiety, preferred monomers are: triethyleneglycol diacrylate and dimethacrylate, diethyleneglycol diacrylate, decanediol diacrylate, ethoxyethoxyethyl acrylate, iso-bornyl acrylate, ethyl 1-acetyl-2-vinyl-1-cyclopropane carboxylate, ethyl 2-vinylcyclopropane-1,1-dicarboxylate and mixtures thereof. Preferred binders for these systems are: polystyrene and copolymers containing at least about 60% styrene.

If crosslinking of the photopolymer is desired, up to about five weight percent of at least one multifunctional monomer containing two or more terminal ethylenically unsaturated groups may be incorporated into the composition. Suitable multifunctional monomers include di-(2-acryloxyethyl)ether of bisphenol A, ethoxylated bisphenol A diacrylate, and the like. A preferred crosslinking is ethoxylated bisphenol A diacrylate.

Other Components

Other components conventionally added to photopolymerizable compositions can be present to modify the physical properties of the film. Such components include: plasticizers, thermal stabilizers, optical brighteners, ultraviolet radiation absorbing material, adhesion modifiers, coating aids, and release agents.

A plasticizer may be present to modify adhesion, flexibility, hardness, and other mechanical properties of the film in a conventional fashion. In general, water insoluble plasticizers are preferred for greater high humidity storage stability, but are not necessary to get improved latitude. When a binder is present, a plasticizer would be selected which is compatible with the binder as well as the ethylenically unsaturated monomer and other components of the composition. With acrylic binders, for example, plasticizers can include dibutyl phthalate and other esters of aromatic acids; esters of aliphatic polyacids, such as diisooctyl adipate; aromatic or aliphatic acid esters of glycols; polyoxyalkylene glycols; aliphatic polyols; alkyl and aryl phosphates; chlorinated paraffins; etc.

Many ethylenically unsaturated monomers are subject to thermal polymerization, especially when stored for long periods or at elevated temperatures. Normally a conventional polymerization inhibitor will be present to improve the storage stability the photopolymerizable composition. The dinitroso dimers described in Pazos, U.S. Pat. No. 4,168,982, may also be useful. Since monomers generally contain thermal polymerization inhibitors added by their manufacturers, it is frequently unnecessary to add additional inhibitor.

Nonionic surfactants may be added to the photopolymerizable composition as coating aids. Typical coating aids are polyethylene oxides, such as Polyox® WSRN, and fluorinated nonionic surfactants, such as Fluorad® FC-430 and Fluorad® FC-431.

Optical brighteners, such as those disclosed in U.S. Pat. Nos. 2,784,183; 3,664,394; and 3,854,950 may be added to reduce distortion due to halation. Ultraviolet radiation absorbing materials are also disclosed in U.S. Pat. No. 3,854,950.

Depending on the application, other inert additives can be employed such as dyes, pigments and fillers. These additives are generally present in minor amounts so as not to interfere with the exposure of the photopolymerizable layer.

Composition

The photoinitiator system must be present in sufficient amount to initiate polymerization of the monomer on exposure to actinic radiation.

The binder, if present, must be present in sufficient amount to form a film when the composition is coated. If the amount of binder is below approximately 25%, or the amount of monomer exceeds approximately 60%, the composition has insufficient viscosity to form a film.

While the composition of the photopolymerizable composition will depend on the intended application, in general, the proportions of ingredients will generally be within the following percentage ranges, based on the total weight of the composition: photoinitiator system (sensitizer, HABI, and chain transfer agent) about 0.3% to about 15%; monomer about 80% to about 99%; binder about 0% to about 90%; and other ingredients about 0% to about 5%. If the composition is to be used as a dry film, the binder should be at least about 25% and the monomer should not exceed about 60%.

The amount of sensitizer present will depend on the wavelength(s) of actinic radiation used for exposure, the absorption spectrum of the sensitizer, and the thickness of the layer of photopolymerizable composition. As described by Thommes and Webers, *J. Imag. Sci.*, 29, 112 (1985), an optical density of 0.43 produces efficient photopolymerization for systems which are developed by washout, such as photoresists. It is generally preferred that the absorption maximum of the sensitizer be matched to the intensity maximum of the source of actinic radiation. In general the sensitizer will comprise about 0.05 to about 1.0% preferably about 0.1% to about 0.50% of the composition.

For photopolymerizable compositions adapted for the preparation of holograms proportions of ingredients will generally be within the following percentage ranges, based on the total weight of the composition: binder 25 to 90%, preferably 45 to 75%; monomer(s), 5 to 60%, preferably, 15 to 50%; plasticizer, 0 to 25%, preferably, 0 to 15%; photoinitiator system, 0.1 to 10%, preferably 1 to 7%; and other ingredients, 0 to 5%, typically 0 to 4%. At high levels of binder addition, exceeding approximately 90%, performance is unduly lost, and the resulting films have diminished values of refractive index modulation. Likewise, levels of monomer(s) used will be at least approximately 5% since lower quantities will not produce films having practical values of refractive index modulation.

Substrates/Coating

The photopolymerizable compositions can be coated onto a wide variety of substrates. By "substrate" is meant any natural or synthetic support, preferable one which is capable of existing in a flexible or rigid form. For example, the substrate can be a metal sheet or foil, a sheet or film of synthetic organic resin, cellulose paper, fiberboard, and the like, or a composite of two or more of these materials.

The particular substrate will generally be determined by the intended application. For example, when printed circuits are produced, the substrate may be a plate which is a copper coating on fiberboard; in the preparation of of lithographic printing plates, the substrate may be anodized aluminum. Specific substrates include alumina-blasted aluminum, anodized aluminum, alumina-blasted polyethylene terephthalate film, polyethylene terephthalate film, e.g., resin-subbed polyethylene terephthalate film, polyvinyl alcohol-coated paper, cross-linked polyester-coated paper, nylon, glass, cellulose acetate film, heavy paper such as lithographic paper, and the like. For the preparation of holograms, polyethylene terephthalate film is preferred.

Exposure

Any convenient source or sources of actinic radiation providing wavelengths in the region of the spectrum that overlap the absorption bands of the photosensitizer can be used to activate photopolymerization. The radiation can be natural or artificial, monochromatic or polychromatic, incoherent or coherent, and for high efficiency should correspond closely to in wavelength to the absorption of the photoinitiator system.

Conventional light sources include fluorescent lamps, mercury, metal additive and arc lamps. Coherent light sources are xenon, argon ion, and ionized neon lasers, as well as tunable dye lasers and the frequency doubled neodymium:YAG laser, whose emissions fall within or overlap the visible absorption bands of the sensitizer.

For the exposure of holographic photopolymer systems coherent light sources, i.e., lasers, are required. Typically ion lasers, which have the required stability and coherence length but operate at a few lines of fixed wavelength, have been used. Since is often desirable to record the hologram or holographic optical element (i.e., a hologram which acts as a diffraction grating, a mirror, a lens, or a combination of optical elements) with the same wavelength actinic radiation which will be used for reconstruction, tunable lasers offer added flexibility of recording a hologram and making a holographic optical element at any desired wavelength or at more than one selected wavelength. One type of tunable laser, the dye laser, can operate at any wavelength from the ultraviolet to the infra-red by the proper choice of pump source and dye medium. The bandwidth of the dye lasers can be narrowed with the use of intracavity etalons resulting in long coherence lengths.

In the preparation of holograms from the compositions of this invention, the hologram is fixed by a second, overall exposure to actinic radiation. If the hologram is a reflection hologram and the binder is poly(vinyl butyral), poly(vinyl acetate), or a copolymer of vinyl acetate with tetrafluoroethylene and/or hexafluoropropylene containing 3 to 25% by weight fluorine, the refractive index modulation of the hologram can be enhanced by heating to 100°-150° C. for about 0.5-3 hours following overall exposure.

Holographic Recording Systems

The general principles are described in a number of references, e.g., "Photography by Laser" by E. N. Leith and J. Upatnieks in *Scientific American*, 212 (6) 24-35 (June, 1965). A useful discussion of holography is presented in "Holography", by C. C. Guest, in *Encyclopedia of Physical Science and Technology*, Vol. 6, pp. 507-519, R. A. Meyers, Ed., Academic Press, Orlando, Fla., 1987.

The object to be imaged is illuminated with coherent light and a light sensitive recording medium is positioned so as to receive light reflected from the object. This beam of reflected light is known as the object beam. At the same time, a portion of the coherent light is directed to the recording medium, bypassing the object. This beam is known as the reference beam. The interference pattern that results from the interaction of the reference beam and the object beam impinging on the recording medium is recorded in the recording medium.

Holograms that are formed by allowing the reference and object beams to enter the recording medium from the same side are known as transmission holograms. Transmission holograms may be produced by methods which are well known in the art, such as disclosed in Leith and Upatnieks, U.S. Pat. Nos. 3,506,327; 3,838,903 and 3,894,787.

Holograms formed by allowing the reference and object beams to enter the recording medium from opposite sides, so that they are traveling in approximately opposite directions, are known as reflection holograms. Reflection holograms may be produced by the on-axis method wherein the beam of coherent radiation is projected through the recording medium onto an object therebehind. In this instance, the reflected object beam returns and interacts with the projected beam in the plane of the recording medium.

Reflection holograms also may be produced by an off-axis method wherein a reference beam is projected on one side of the recording medium and an object beam is projected on the reverse side of the medium. In this, instance, the original beam of coherent radiation is split into two portions, one portion being projected on the medium and the other portion being manipulated to project on the object behind the medium. Reflection holograms produced by an off-axis process are disclosed in Hartman, U.S. Pat. No. 3,532,406.

The theory for thick hologram gratings and mirrors, generally known as the "coupled wave theory", has been developed by H. Kogelnik, *Bell Syst. Tech. J.*, 48, 2909-2947 (1969). According to this theory, a holographic mirror can be characterized by its refractive index modulation. Using this theory the refractive index modulation of a mirror can be calculated from its reflection efficiency, that is, the percent of incident radiation reflected; thickness; and the angle and wavelength of the probe radiation. To determine the refractive index modulation for a particular recording material, a holographic mirror is formed in the material, and the thickness and the maximum efficiency of the hologram determined. Since refractive index modulation is thickness, angle, and wavelength independent, it is a convenient parameter to use in comparing holographic recording materials.

Industrial Applicability

The photopolymerizable compositions of this invention show good visible light sensitization which allows them to be exposed with a variety of visible light sources. The broad sensitization range enables polymeric images, which may be further processed by development to produce resist images, or other relief images, to be formed. These compositions are useful in printing plates for offset and letter press, engineering drafting films, as well as photoresists in liquid or dry film form for making printed circuits or in chemical milling or in solder masks. Certain compositions of this invention are particularly useful for the formation of holograms in which sensitivity to visible lasers is required. These holograms can also be used as displays, holographic optical elements, holographic notch filters, etc. Other specific uses for the compositions of this invention as well as the holograms prepared therefrom will be evident to those skilled in the art.

Syntheses

The sensitizers are readily prepared by base catalyzed condensation of the corresponding aldehydes with the corresponding 3-methyl-5,5-dialkyl-2-cyclohexene-1-one. A preferred cyclohexeneone for use in these syntheses is isophorone. The synthesis of sensitizer S-1 is given in G. Kabas, *Tetrahedron*, 22, 1213-1218 (1966) and R. Lemke, *Chem. Ber.*, 103, 1168-1173 (1970).

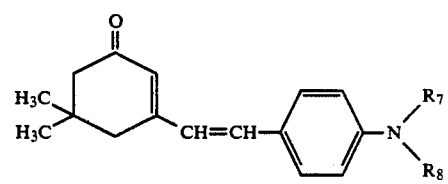

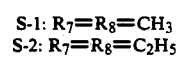

-continued

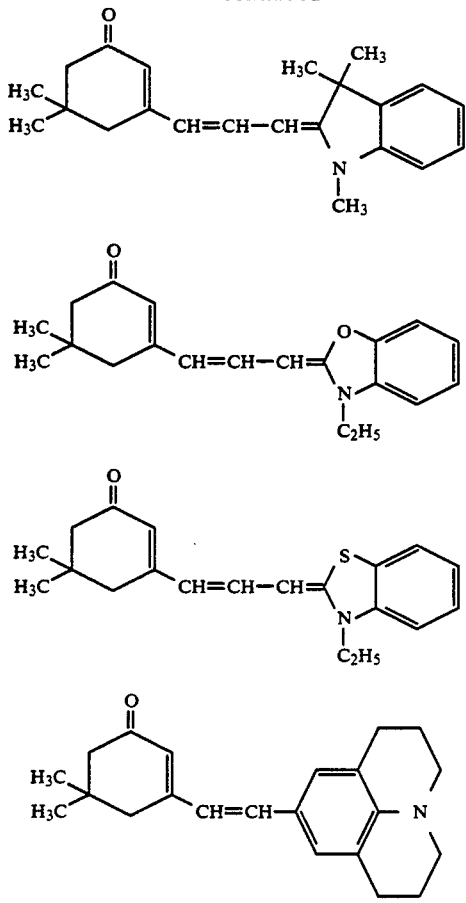

The advantageous properties of this invention can be observed by reference to the following examples which illustrate, but do not limit, the invention.

EXAMPLES

Glossary

| | EXAMPLES GLOSSARY |
|---|---|
| o-Cl-HABI | Biimidazole, 2,2'-bis[o-chlorophenyl]-4,4',5,5'-tetraphenyl-; CAS 1707-68-2 |
| FC-430 | Fluorad ® FC-430; fluoroaliphatic polymeric esters; CAS 11114-17-3; 3M Company, St. Paul, MN |
| Fischer's Aldehyde | Acetaldehyde (1,3-dihydro-1,3,3-trimethyl-2H-indol-2-ylidene)- |
| 9-JA | 9-Julolidine carboxaldehyde; 9-carboxaldehyde, 2,3,6,7-tetrahydro-1H,5H-benzo[i,j]quinolizine; CAS 33985-71-6 |
| MMT | 4-Methyl-4H-1,2,4-triazole-3-thiol; CAS 24854-43-1 |
| NVC | N-Vinyl carbazole; 9-vinyl carbazole; CAS 1484-13-5 |
| Photomer ® 4039 | Phenol ethoxylate monoacrylate; CAS 56641-05-5; Henkel Process Chemical Company |
| Sartomer 349 | Ethoxylated bisphenol A diacrylate; CAS 24447-78-7; Sartomer Company, West Chester, PA |
| Sensitizer S-3 | 2-Cyclohexen-1-one, 5,5-dimethyl-3-[3-(1,3-dihydro-1,3,3-trimethyl-2H-indol-2-ylidene)propylidene]- |
| Sensitizer S-4 | 2-Cyclohexen-1-one, 5,5-dimethyl-3-[3-(3-ethyl-2(3H)-benzoxazolylidene)-propylidene]- |
| Sensitizer S-5 | 2-Cyclohexen-1-one, 5,5-dimethyl-3-[3-(3-ethyl-2(3H)-benzothiazolylidene)-propylidene]- |
| Sensitizer S-6 | 2-Cyclohexen-1-one, 5,5-dimethyl-3-[2-(2,3,6,7-tetrahydro-1H,5H-benzo[i,j]-quinolizin-9-yl)ethenyl]- |
| TFE/VAc | Poly(tetrafluoroethylene/vinylacetate) copolymer: (23:77 by weight wt %; inherent viscosity 1.52 dL/g in THF) |
| Vinac ® B-100 | Poly(vinyl acetate); M.W. 350,000; CAS 9003-20-7; Air Products, Allentown, PA |

GENERAL PROCEDURES

All commercially available components were used as received from suppliers without further purification.

Coating solutions were prepared in amber bottles under dim light by adding solvent (80–85% of total solution by weight) and nonvolatile coating ingredients (15–20%) and mixing with a mechanical stirrer until the ingredients completely dissolved. The solvent was a mixture of dichloromethane (90–95% of total solvent by weight), 2-butanone (0–5%), and methanol (5%).

Solutions were coated onto a 50 micron thick clear film support of polyethylene terephthalate at a speed of 8 ft/min (4 cm/sec) using a Talboy web-coater equipped with a 6-mil (150 micron) or 8-mil (200 micron) doctor knife, 12 ft (3.7 m) drier set at 50°–70° C., and a laminator station. A coversheet of 25 micron polyethylene terephthalate or 25 micron polypropylene was laminated to the coatings as they exited the drier. Dry coating thickness ranged between 8 and 27 microns. Coated samples were stored in black polyethylene bags at room temperature until used.

Coated film with both the film support and coversheet intact was cut into 10×13 cm sections. The coversheet was removed, and the film was then mounted by laminating the soft, tacky coating onto a clear glass plate. The film support was left in place during exposure and processing operations.

Coating samples mounted on glass plate were evaluated by recording a series holographic mirrors and determining hologram reflection efficiency as a function of exposure and wavelength. Holographic mirrors were formed by first tightly clamping the coating sample-plate between a clear glass cover-plate and a front surface aluminized-glass mirror, with thin xylene layers between. The thin layer of xylene served to optically couple the glass and mirror to the film. Then the sample-plate was exposed by a collimated 488 nm argon-ion laser beam oriented perpendicular to the film plane and passing, in order, through the glass cover-plate, xylene layer, film support, coating, glass sample-plate, and xylene layer and then reflecting back onto itself off the mirror. The laser beam had a 2.0 cm diameter and an intensity of 10 mW/cm². A series of sixteen holographic mirrors were recorded, each at a separate non-overlapping position on the sample-plate, with the laser exposure time incrementally varied using a computer controlled shutter positioned in the laser beam.

After the laser exposure series was complete, the glass cover-plate, aluminum mirror, and xylene layers were removed and the coating was overall exposed to ultraviolet and visible light from a Theimer-Strahler

5027 mercury-arc photopolymer lamp (Exposure Systems Corp., Bridgeport, Conn.) mounted in a Douthitt DCOP-X exposure unit (Douthitt Corp., Detroit, Mich.). The coating was then thermally processed by heating the sample-plate at 100°-120° C. for 30-60 min in a forced-air convection oven. The transmission spectrum of each holographic mirror was then recorded using a standard double-beam scanning spectrophotometer (Perkin Elmer model Lambda-9) with the sample beam oriented perpendicular to the plane of the sample-plate. Maximum reflection efficiency and peak reflection wavelength for each holographic mirror was measured from their transmission spectra. Graphs of reflection efficiency at the peak reflection wavelength versus total laser exposure were used to determine photospeed, which is defined here as the minimum laser exposure required to obtain maximum holographic reflection efficiency. Refractive index modulation was calculated from hologram reflection efficiency, reflection wavelength, and coating thickness using the well-known coupled wave theory (H. Kogelnik, *Bell. Syst. Tech. J.*, 48, 2909-2947, 1969).

The syntheses for sensitizers S-3, S-4, S-5, and S-6, described in Examples 1-4, illustrates the preparation of the sensitizers of this invention. Other sensitizers may be prepared by analogous procedures.

EXAMPLE 1

Sensitizer S-3: To a solution of 7.5 g (37.3 mmol) of Fischer's aldehyde, prepared from 2-methylene-1,3,3-trimethylindoline and POCl3 in N,N-dimethylformamide by the procedure of H. Fritz, *Chem. Ber.*, 92, 1809-1817 (1959), and 10.4 g (75.4 mmol) isophorone in 60 mL of ethyl alcohol, was added 3.75 g (46.9 mmol) of a 50% aqueous sodium hydroxide solution. The resulting reaction mixture was heated at reflux for 37 hours. The reaction mixture was poured into 300 mL of water, neutralized with 1.0M hydrochloric acid, and extracted three times with 100 mL of ether. The separated ether layers were combined and washed with saturated sodium chloride, dried over anhydrous magnesium sulfate, filtered, and evaporated to give 15.1 g of crude product.

The crude product was chromatographed through a column of silica gel with a gradient of ethyl acetate in hexane according to the procedure of L. M. Harwood, *Aldrichimica Acta*, 18, 25 (1985). The fractions eluted with 40% through 52% ethyl acetate were combined and rechromatographed using the procedure of W. C. Stille, *J. Org. Chem.*, 43, 2923 (1978), using 10% ethyl acetate and 90% chloroform as eluent. This gave 0.40 g of Sensitizer S-3, m.p. 68°-72° C. (2 max=442 nm, E=43,000 in $CH_2Cl_2$) in an overall yield of 3%.

EXAMPLE 2

Compound I: With care being taken to exclude moisture, 800 mL of N,N-dimethylformamide was chilled to between 0° and 5° C. and 65 g (0.425 mol) of POCl3 was added over a 15 min period. To the resulting solution was added 100 g (0.346 mol) of 3-ethyl-2-methylbenzoxazolium iodide. The reaction mixture was stirred at between 5° and 15° C. while 65 g (0.821 mol) of pyridine was added over 45 min.

The reaction mixture was then warmed to room temperature and quenched by gradually adding 80 mL of water over 15 min while maintaining the reaction temperature at about 35° C. with cooling. The reaction mixture was stirred for 30 min and 540 g (3.25 mol) of potassium iodide dissolved in 820 mL water was added over 30 min to precipitate product as the iodide salt. The reaction temperature rose to 40° C. during this time. The resulting slurry was chilled in an ice bath and the product collected by filtration. The product was washed successively with ice water, cold methanol, and ether, and dried in vacuo at 55° C. to give 107.3 g of Compound I (90% yield); m.p. 275°-276° C.

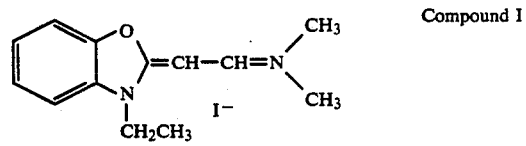

Compound I

Sensitizer S-4: To a mixture of 5.0 g (14.5 mmol) of Compound I and 2.2 g (15.8 mmol) isophorone, was added 20 mL (20.0 mmol) of a 1.0M potassium t-butoxide in tetrahydrofuran, with care being taken to exclude moisture. The resulting reaction mixture was then stirred at room temperature for 90 min. The reaction mixture was then poured into a stirred mixture of 50 mL of dichloromethane and 200 mL of water and neutralized with 1.0M hydrochloric acid. The dichloromethane layer was separated and washed with saturated sodium chloride, dried over anhydrous magnesium sulfate, filtered, and evaporated to give 4.5 g of crude product. The entire crude product was chromatographed through a column of silica gel with a gradient of ethyl acetate in hexane according to the procedure of Harwood, cited above. The fraction eluting with 68% ethyl acetate content gave, upon evaporation, 0.6 g of crude Sensitizer S-4. Crude sensitizer S-4 was rechromatographed by the procedure of Stille, cited above, using 20% ethyl acetate and 80% chloroform as eluent This gave 0.28 g of Sensitizer S-4, m.p. 140°-143° C. (2 max=443 nm, E=49,000 in $CH_2Cl_2$) in an overall yield of 6%.

EXAMPLE 3

Compound II, mp 282°-283° C., was prepared in 89% yield from 3-ethyl-2-methylbenzothiazolium p-toluenesulphonate and POCl3 in N,N-dimethylformamide as in the preparation of Compound I.

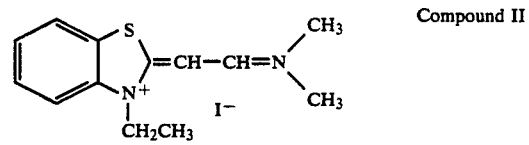

Compound II

Sensitizer S-5: To a solution of 8.3 g (23.1 mmol) of Compound II and 3.5 g (25.4 mmol) isophorone in 42 mL of anhydrous methanol, was added 6.2 g (28.8 mmol) of a 25% methanolic sodium methoxide solution, with care being taken to exclude moisture. The resulting reaction mixture was then heated at reflux for 23 hours. The reaction mixture was dissolved in 400 mL of 0.25M hydrochloric acid, treated with charcoal, and filtered through Celite. While maintaining good stirring throughout, the filtrate was neutralized with 1.0M aqueous sodium hydroxide, precipitating crude product as a fine slurry. The solids were collected by filtration, washed with water, and air dried overnight to obtain 4.7 g of crude product. The crude product was chromatographed through a column of silica gel by eluting with a gradient of ethyl acetate in hexane according to the procedure of Harwood, cited above. Fractions eluting with 80 and 90% ethyl acetate contained Sensitizer S-5. They were combined to give, upon evaporation, 0.7 g of Sensitizer S-5, m.p. 86°–89° C. (2 max=464 nm, E=42,000 in $CH_2Cl_2$) in an overall yield of 11%.

EXAMPLE 4

Sensitizer S-6: To a solution of 6.0 g (32.6 mmol) of 9-JA (prepared by the formylation of julolidine with phosphorous oxychloride in N,N-dimethylformamide as described in Monroe, U.S. Pat. No. 4,987,230) and 4.5 g (29.7 mmol) isophorone in 50 mL of ethyl alcohol, was added 3.0 g (37.5 mmol) of a 50% aqueous sodium hydroxide solution. The resulting reaction mixture was heated at reflux for 6 hours. The reaction mixture then cooled slowly overnight to room temperature. A precipitate formed which was collected by filtration, washed sparingly with chilled ethyl alcohol, and dried in vacuo at 55° C. to give 4.6 g of crude product, m.p. 147°–150° C. A 3.0 g portion of crude product was recrystallized from a mixture of 40 mL toluene and 80 mL hexane to obtain 1.9 g of Sensitizer S-6 as golden yellow crystals, m.p. 151°–153° C. (2 max=433 nm, E=35,000 in $CH_2Cl2$).

EXAMPLES 5–8

These examples demonstrates the utility of Sensitizers S-3 to S-6 as sensitizers in photopolymerizable compositions. The TFE/VAc binder was prepared as described in Trout, U.S. Pat. No. 4,963,471.

Coating solutions were prepared consisting of 4.88 g TFE/VAc 1.65 g Photomer 4039; 0.450 g NVC; 0.225 g Sartomer 349; 0.075 g MMT; 0.188 g o-Cl HABI; dye sensitizer as indicated in Table I; 38.3 g dichloromethane, 2.13 g methanol, and 2.13 g 2-butanone. The solutions were coated with a 6-mil (150 micron) doctor knife, dried, and imaged at 488 nm to record a series of reflection holograms. Dry coating thickness ranged between 8 and 10 microns. The holograms were exposed to ultraviolet and visible light and then heated at 120° C. for 60 min and analyzed for reflection efficiency, refractive index modulation, and photospeed as described in the General Procedures. Results are given in Table 1.

EXAMPLE 9

This example demonstrates the utility of Sensitizer S-6 as a sensitizer in a photopolymerizable composition.

A coating solution was prepared consisting of 26.4 g Vinac® B-100; 6.82 g Photomer 4039; 3.14 g NVC; 1.20 g of Sartomer 349; 0.852 g MMT; 1.48 g o-Cl HABI; 0.08 g FC-430; 0.12 g Sensitizer S-6; 152 g dichloromethane, and 8.0 g methanol. The solution was coated with a 8-mil (200 micron) doctor knife, dried, and imaged at 488 nm to record a series of reflection holograms. Dry coating thickness was 27 microns. The holograms were exposed to ultraviolet and visible light and then heated at 100° C. for 30 min and analyzed for reflection efficiency, refractive index modulation, and photospeed as described in the General Procedures. Results are given in Table 1.

TABLE 1

| Exp. | Sensitizer | Amt. (g) | Photospeed ($mJ/cm^2$) | $RE^a$ (%) | Wavelength$^b$ (nm) | $RIM^c$ |
|---|---|---|---|---|---|---|
| 1 | S-3 | 0.0150 | 70 | 98.4 | 478 | 0.042 |

TABLE 1-continued

| Exp. | Sensitizer | Amt. (g) | Photospeed ($mJ/cm^2$) | $RE^a$ (%) | Wavelength$^b$ (nm) | $RIM^c$ |
|---|---|---|---|---|---|---|
| 2 | S-4 | 0.0375 | 100 | 99.6 | 477 | 0.050 |
| 3 | S-5 | 0.0375 | 100 | 98.5 | 477 | 0.047 |
| 4 | S-6 | 0.0600 | 21 | 99.3 | 479 | 0.049 |
| 5 | S-6 | 0.1200 | 13 | 99.99 | 481 | 0.030 |

$^a$Reflection efficiency
$^b$Wavelength of maximum reflection
$^c$Refractive index modulation Having described the invention, we now claim the following and their equivalents:

1. A photopolymerizable composition comprising:
   (1) at least one ethylenically unsaturated monomer capable of free radical initiated addition polymerization; and
   (2) a photoinitiator system, capable of being activated by actinic radiation, said photoinitiator system comprising:
   (a) a hexaarylbisimidazole;
   (b) a chain transfer agent;
   (c) a sensitizer, said sensitizer selected from the group consisting of:

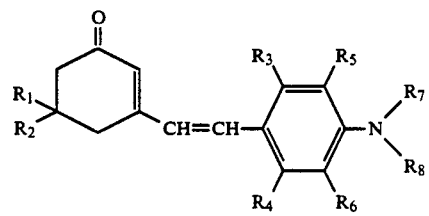

A wherein:
$R_1$ and $R_2$ are independently alkyl from 1 to 4 carbon atoms;

$R_3$ and $R_4$ are independently hydrogen, alkyl of 1 to 6 carbon atoms, or alkyloxyl of 1 to 6 carbon atoms;

$R_5$ is hydrogen or methyl and $R_7$ is alkyl from 1 to 6 carbon atoms, or ($R_5+R_7$) are —($CH_2$)$_2$— or —($CH_2$)$_3$—;

$R_6$ is hydrogen or methyl and $R8$ is alkyl from 1 to 6 carbon atoms, or ($R_6+R_8$) are —($CH_2$)$_2$— or —($CH_2$)$_3$—, with the proviso that ($R_5+R_7$) and ($R_6+R_8$) may not be —($CH_2$)$_2$— at the same time; and

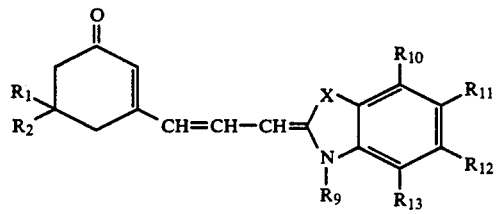

B wherein:
$R_1$ and $R_2$ are independently alkyl from 1 to 4 carbon atoms;

X is O, S, $NR_{14}$, or $CR_{15}R_{16}$, where $R_{14}$, $R_{15}$, and $R_{16}$ are each an alkyl group of 1 to 6 carbon atoms or substituted or unsubstituted phenyl;

$R_9$ is a substituted or unsubstituted alkyl group of 1 to 7 carbon atoms or substituted or unsubstituted phenyl;

$R_{10}$, $R_{11}$, $R_{12}$, and $R_{13}$ are each independently hydrogen, substituted or unsubstituted alkyl and alkyoxyl of 1 to 6 carbon atoms, halogen, or substituted or unsubstituted phenyl; or ($R_{10}$ and $R_{11}$), ($R_{11}$ and $R_{12}$), or ($R_{12}$ and $R_{13}$) are joined to form a six-membered substituted or unsubstituted aromatic ring;

wherein said photoinitiator system is present in an amount sufficient to initiate polymerization of said monomer on exposure to actinic radiation.

2. The composition of claim 1 additionally comprising a binder, wherein said binder is present in sufficient amount to form a film when said composition is coated.

3. The composition of claim 2 wherein $R_1$ and $R_2$ are methyl.

4. The composition of claim 3 wherein said sensitizer has structure A; and ($R_5+R_7$) and ($R_6+R_8$) are each $-(CH_2)_3-$.

5. The composition of claim 3 wherein said sensitizer has structure B, where X is O, S, or $CR_{15}R_{16}$, wherein $R_{15}$ and $R_{16}$ are each methyl; $R_9$ methyl, ethyl, or benzyl; and $R_{10}$, $R_{11}$, $R_{12}$, and $R_{13}$ are each independently hydrogen, methyl, methoxy, or chloro.

6. The composition of claim 5 wherein $R_9$ is methyl or ethyl; and $R_{10}$, $R_{11}$, $R_{12}$, and $R_{13}$ are each hydrogen.

7. The composition of claim 2 wherein either said monomer or said binder comprises one or more moieties selected from the group consisting of (1) aromatic moieties selected from the group consisting of (i) substituted or unsubstituted phenyl, (ii) substituted or unsubstituted naphthyl, and (iii) substituted or unsubstituted heterocyclic aromatic moieties having up to three rings; (2) chlorine; (3) bromine, and mixtures thereof; and the other of said monomer and said binder is substantially free of said moiety or moieties.

* * * * *